United States Patent [19]

Mlinko et al.

[11] 3,945,797
[45] Mar. 23, 1976

[54] PROCESS AND APPARATUS FOR MEASURING THE ISOTOPE CONTENT OF SUBSTANCES LABELLED WITH $^3$H OR $^3$H AND $^{14}$C ISOTOPES

[75] Inventors: Sándor Mlinkó; Dezsö Bánfi; István Gács; Károly Payer; László Ötvös; Zoltán Vargay; Emilia Dobis née Farkas; Tivadar Palágyi, all of Budapest, Hungary

[73] Assignee: Chinoin Gyogyszer es Vegyeszeti Termekek Gyara RT., Budapest, Hungary

[22] Filed: Feb. 5, 1973

[21] Appl. No.: 329,605

[30] Foreign Application Priority Data
Feb. 9, 1972 Hungary .......................... MA2317

[52] U.S. Cl. ........ 23/230 PC; 23/232 R; 23/253 PC; 23/254 R
[51] Int. Cl.$^2$ .................. G01N 23/00; G01N 31/12
[58] Field of Search ........ 23/230 PC, 232 C, 232 R, 23/253 PC, 262, 254 R; 250/302, 303

[56] References Cited
UNITED STATES PATENTS

| | | | |
|---|---|---|---|
| 3,226,197 | 12/1965 | Lewis | 23/253 PC X |
| 3,304,159 | 2/1967 | Hinsvark | 23/232 C |
| 3,506,402 | 4/1970 | Simon | 23/230 PC |
| 3,622,276 | 11/1971 | Haahti et al. | 23/230 PC X |
| 3,679,366 | 7/1972 | Benson et al. | 23/232 C X |
| 3,682,598 | 8/1972 | Kaartinen | 23/253 PC X |
| 3,726,646 | 4/1973 | Kravetz et al. | 23/230 B X |
| 3,832,137 | 8/1974 | Mlinko et al. | 23/232 R X |

Primary Examiner—Morris O. Wolk
Assistant Examiner—Timothy W. Hagan

[57] ABSTRACT

A process for measuring the isotope content of substances containing $^3$H or $^3$H and $^{14}$C isotopes in the gas phase, by converting the hydrogen content of the sample into water and the carbon content of the sample to a gaseous substance in simultaneous oxidation processes, separating the formed water and carbon dioxide, reconverting the $^3$H content of the water into gaseous form, introducing the gases containing $^3$H and possibly also $^{14}$C separately into a detecting unit, and determining the radioactivity of said gases, in which the tritium content of the water carrying the $^3$H radioactivity is bonded on a contact catalyst capable of water retention or adsorption and containing activated hydrogen, the gaseous mixture, containing also $^{14}CO_2$ when a sample of $^{14}$C content is analyzed, is removed and, optionally after purification, is fed into a detecting unit together with a counting gas, then the tritium adsorbed on the surface of the catalyst is continuously converted into gas phase by exchange reaction with an appropriate gas flow and is fed into a detecting unit in unchanged state, or in the form of a compound prepared from it by chemical reaction.

7 Claims, 3 Drawing Figures

|  | $S_1$ | $S_2$ | $S_3$ | $S_4$ | $S_5$ | $S_6$ | $S_7$ | $S_8$ | $S_9$ | $S_{10}$ | $S_{11}$ | $S_{12}$ |
|---|---|---|---|---|---|---|---|---|---|---|---|---|
| I. | ▨ | ▨ | ▨ | ▨ | ▨ | ▨ | ▨ | ▨ | ▨ | ▨ | ▨ | ▨ |
| II. |  | ▨ | ▨ | ▨ |  | ▨ |  | ▨ |  |  | ▨ |  |
| III. | ▨ | ▨ |  |  | ▨ | ▨ | ▨ | ▨ | ▨ | ▨ | ▨ | ▨ |
| IV. | ▨ | ▨ | ▨ | ▨ | ▨ | ▨ | ▨ | ▨ |  |  | ▨ |  |
| V. | ▨ |  | ▨ | ▨ | ▨ |  | ▨ | ▨ | ▨ | ▨ |  | ▨ |
| VI. | ▨ | ▨ |  |  | ▨ | ▨ | ▨ | ▨ | ▨ | ▨ | ▨ | ▨ |
| VII. |  | ▨ | ▨ | ▨ |  | ▨ | ▨ |  | ▨ |  | ▨ |  |

Fig.3

PROCESS AND APPARATUS FOR MEASURING THE ISOTOPE CONTENT OF SUBSTANCES LABELLED WITH $^3H$ OR $^3H$ AND $^{14}C$ ISOTOPES

This invention relates to a process for measuring the isotope content of substances containing $^3H$ or $^3H$ and $^{14}C$ isotopes — first of all of organic compounds and samples of biological origin — in the gas phase, by converting the hydrogen content of the sample into water and, the carbon content of the sample to a gaseous substance, preferably to carbon dioxide gas, in sumultaneous oxidation processes, separating the formed water and carbon dioxide, reconverting the $^3H$ content of the water into gaseous form, introducing the gases containing $^3H$ and possibly also $^{14}C$ separately into a detecting unit, and determining the radioactivity of said gases. The invention relates further to an apparatus for carrying out the above process.

The tracer technique using radioactive isotopes is an important, indispensable investigation method in theoretical and practical research work connected to biology, biochemistry and related fields. The application of tracer methods in these fields relies first of all on the organogen elements and, among these, most frequently on the hydrogen isotope of mass number 3 and carbon isotope of mass number 14. It is well known that the analysis of radioactive substances containing these isotopes is still the most complicated and most difficult task of the nuclear measuring technique.

Recently, on the field of practical use, first of all the pharmaceutical industry and pharmaceutical research work, agricultural chemical research and food industry have become the most extensive utilizers of the isotopes mentioned above.

In the pharmaceutical research work the tracer technique is used for different pharmacological, microbiological, pharmacobiochemical, preparation-technical and technological routine examinations, while in the agricultural chemical research it is used for the different plant- and animal-physiological investigations in studies on the absorption, accumulation and natural decomposition of herbicides, insecticides and preserving agents, as well as in toxicological investigations connected to the above agents.

The behaviour of pharmaceutical products or of chemicals, used in the agriculture and food industry, in the living organism, the mechanism of their transport processes, e.g. the mechanism of absorption, distribution, excretion or accumulation, the metabolic changes of the products, etc. can be established by serial examinations using indicator compounds labelled with radioactive isotopes.

Due to the recognition of the harmful effects of foreign substances entering the living oganisms together with pharmaceuticals and foodstuffs, the marketing of pharmaceutical products and chemicals used in agriculture or food industry (e.g. herbicides, preserving agents, etc.) is regulated by orders prescribing more and more severe examinations all over the world. In the development of such examinations the compulsory introduction of radioisotopic tracer-indication methods is playing a role of rapidly growing importance. Thus, e.g., according to an order of WHO in 1966, a compulsory radoisotopic pharmacological examination is prescribed before releasing a new pharmaceutical product to the market.

Since in the majority of these examinations indicator compounds labelled with $^3H$ and $^{14}C$ isotopes are to be used, the examinations of the applied related research fields rendered now compulsory the urgent development of processes and the marketing of measuring devices applicable for the accurate and rapid measurement of $^3H$ and $^{14}C$ isotopes.

The use of tracer-technique utilizing soft $\beta$-isotopes in several important fields of practical research and application is hindered first of all by the lack of high-capacity measuring devices for the determination of the radioactivity of $^3H$ and $^{14}C$ isotopes with reliable accuracy and sensitivity, by the shortcomings of the equipment marketed so far, as well as by the extremely high price of the equipment. At the same time just these new fields of application have raised the new demands against isotope analysis that could hardly or even not be fulfilled by the equipment marketed so far.

The unusually high number of samples requires the automation of $^{14}C$ and $^3H$ measuring methods; furthermore, due to the small amount of radioactive substances contained in samples of widely different kind, and for making possible the efficient counting of low-energy $\beta$-particles, extremely sensitive detecting methods are required. Even the separate solution of these tasks poses serious technical problems.

As far as automation is concerned, liquid scintillation counting methods have been developed most rapidly. Counting equipment ($\beta$-spectrometers) of completely automated operation, now available in the international market, are able to handle several hundreds of samples and to analyze them fully automatically with a more or less acceptable accuracy, and meet almost completely the needs of activity measurement in several fields of soft $\beta$-isotope indication examinations. A common disadvantage, however, of this equipment is that the mechanism and partial processes of scintillation, as a physical phenomenon upon which the counting is based, are not yet cleared Consequently, the sensitivity and counting efficiency of such equipment depend on the physical and chemical characteristics of the substances to be measured. The efficiency of counting is reduced in heterodisperse systems by self-absorption, and in homogeneous solutions by the inestimable colour and concentration quenching effects, arising from the physical and chemical characteristics of the solvent and the substances dissolved therein. On the other hand, a false increase of the counting efficiency may occur in some cases due to phosphorescence and fluorescence phenomena in the samples. The correction of these factors increasing or decreasing counting efficiency can only be carried out with great difficulties, and even the approximate correction requires the use of complicated and expensive equipment (computers).

Particular difficulties arise if liquid-scintillation counting methods are to be used for the isotope analysis of various types of biological samples produced by the routine examinations of pharmaceutical and agricultural chemical research (e.g. residues of plant or animal organs). Even the preparation of the counting solution (i.e. the solubilization) is a time-consuming, laboursome process requiring various manipulations that cannot be automated, and containing several error sources. A great number of the biological samples are colored, frequently insoluble, or form a heterodisperse colloid solution. At the selection of a suitable liquid scintillator, including also the solvents, solubilizing agents, as well as primary and secondary scintillators, the external characteristics, physical and chemical, but first of all the scintillation properties of the substances should be taken into account. Furthermore the possible colour- and different concentrationquenching effects should be considered, and suitable correction methods should be chosen. These correction manipulations require complicated and time-consuming calculation work. It follows from the above that due to the broad range of materials and the variety of samples, the analysis of a sample often needs separate preliminary investigations.

The reliable isotope analysis of samples simultaneously labelled with $^3H$ and $^{14}C$ isotopes can hardly be solved by liquid scintillation technique. The efficiency correction requires even more sophisticated calculations in this case. The simultaneous determination of $^3H$ and $^{14}C$ isotopes requires multichannel counters, and can be carried out only by energy discrimination methods. Consequently, the counting efficiency drops to the half or even to a smaller fraction of the original value.

In order to overcome the above-discussed difficulties arising at the liquid scintillation activity measurement methods attempts have been made to develop gas phase counting methods for the determination of soft -62 -radiating isotopes of samples containing $^3H$ and $^{14}C$. In these methods the tritium or carbon content of solid or liquid samples is converted into a gas. The gas sample is filled into counter tubes or ionization chambers of flow system, operating in the GM- or proportional range, and the radioactivity is determined in the gas phase.

The advantage of counting carried out in tubes of flow system lies in the fact that a nearly absolute intensity is measured, without window-effect, i.e. counting efficiency is almost 100 per cent. Irrespectively of the type of the sample, the measurement is carried out always on the same gas (e.g. HT, $TH_2C-CH_2T$, $^{14}CO_2$, $^{14}CO$ or $^{14}CH_4$), the evaluation is simple, no correction calculations are necessary, error sources are limited, and the reproducibility of the measurements is favourable. The gas phase $^{14}C$ and $^3H$ counting procedures known so far, however, have the common disadvantage that the preparation of the specimen prior to the counting, i.e. the conversion of the carbon or tritium content of the sample to the specimen gas, is a time-consuming process which depends on the skill and practice of the operator, and the procedure requires extremely complicated equipments. Namely, the gas samples should be purified very carefully, which involves the freezing out, isolation, and further chemical transformation of HTO or $^{14}CO_2$. Before the measurement of the next sample the equipment should always be carefully decontaminated in order to exclude memory effect, which operation is, mainly in the case of tritium determination, an extremely difficult, practically almost insoluble task. The complete process consists of individual, intermittent partial processes to be carried out manually, and so it is extremely time- and labour-consuming.

The simultaneous determination of $^3H$ and $^{14}C$ isotopes in the same sample cannot be solved by the gas phase soft $\beta$-counting, either. In all the measuring methods known until now these two isotopes have been determined in separate equipments from separate samples. The known measuring methods, almost without exception, are either based on energy discrimination or separate samples are used, so a separate operation or equipment should be applied if both of the above two isotopes are to be determined from the same sample. This, obviously, results in the reduction of counting efficiency in the first case, and leads to extremely complicated and time-consuming manipulatons in the second case.

The invention aims at the elaboration of a process and equipment being free of the disadvantages of the known ones and making possible the highly accurate and sensitive measurement of the radioactivity of samples containing tritium or tritium and $^{14}C$ isotope, optionally without any manual intervention, i.e., in a fully automated operation.

The invention is based on the recognition that in the gas-phase measurement technique one of the main problems is the purification and quantitative isolation of the active gas from the gas mixture forming upon the conversion of the sample into gas phase. Now we have found that the total $^3H$ amount of the water formed at the oxidation of the hydrogen content of the sample can be absorbed on special contact catalysts within certain temperature limits, while all the other gases formed in the burning procedure can be removed, and the tritium isolated in the above manner can continuously be converted into gas phase using an appropriate gas flow.

This invention is based further on the discovery that when samples containing both $^{14}C$ and $^3H$ isotopes are to be analyzed, the $^{14}C$ activity of the gas mixture separated from the total tritium content of the sample can be measured separately and independently of the tritium also with almost 100% efficiency; consequently, when determining the isotope content of the sample the use of energy discrimination in the measuring of radioactivity can be omitted.

The invention is based finally on the recognition that by using an appropriate gas or gas mixture as counting gas, or by converting the hydrogen gas sample, via an appropriate chemical reaction, to a compound which can be used as counting gas even in itself, the obtained gaseous sample can also be used in the determination of activity without any special purification step. It was, in fact, also this observation that gave the clue to the complete automation of the measurement, i.e. to the operation mode where, in a given equipment, the measurement can be carried out without manual intervention, merely by the automatic operation of valve systems.

Accordingly, this invention relates to a process for measuring the isotope content of substances containing $^3H$ or $^3H$ and $^{14}C$ isotopes — first of all of organic compounds and samples of biological origin — in the gas phase, by converting the hydrogen content of the sample into water and the carbon content of the sample to a gaseous substance, preferably to carbon dioxide gas, in simultaneous oxidation processes, separating the formed water and cabon dioxide, reconverting the $^3H$ content of the water into gaseous form, introducing the gases containing $^3H$ and possibly also $^{14}C$ separately into a detecting unit, and determining the radioactivity of said gases. According to the invention one proceeds as follows: the tritium content of the water carrying the $^3H$ radioactivity is bonded on a contact catalyst capable of water retention or adsorption and containing activated hydrogen, preferably on aluminium oxide and/or aluminium hydrosilicate, the gaseous mixture, containing also $^{14}CO_2$ when a sample of $^{14}C$ content is analyzed, is removed and, optionally after purification, is fed into a detecting unit together with a counting gas, then the tritium adsorbed on the surface of the catalyst is continuously converted into gas phase by exchange reaction with an appropriate gas flow, preferably hydrogen flow, and is fed, optionally together with a counting gas, preferably a gaseous hydrocarbon or a mixture of such gases, into a detecting unit in unchanged state, or in the form of a compound prepared from it by chemical reaction.

Alkali metal, alkaline earth metal or earth metal oxides, silicates, sulphates, carbonates hydrosilicates or substances containing such compounds, such as calcined clay minerals, molecular sieves, zeolites, etc., containing hydrogen capable of entering exchange reaction, can be preferably used as contact catalysts.

Tritium is firmly bonded to the surface of the contact catalyst even when transferring high amounts of gases, with the exception of certain special gases or gas mixtures, which are used according to the invention just for the liberation of gaseous tritium.

According to an advantageous method of implementation of the invention the liberation of gaseous tritium from the surface of the catalyst is continuously carried out with hydrogen gas, utilizing the following exchange reaction:

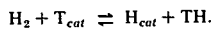

$$H_2 + T_{cat} \rightleftarrows H_{cat} + TH.$$

The exchange reaction may also proceed with other gases containing activated hydrogen, such as $H_2S$; these gases have, however, no advantages over hydrogen in the subsequent operations.

The gas obtained in the above reaction, containing the total $^3H$ amount of the sample, can be led directly into the detecting unit together with a counting gas, preferably with a gaseous hydrocarbon or a mixture of such gases or it may be converted in a chemical reaction, and the converted gas can be led into the detecting unit in itself, or together with a counting gas.

In compliance with a preferred variant of the process according to the invention, the hydrogen gas sample containing $^3H$ is reacted with an unsaturated hydrocarbon, preferably butadiene, in the presence of a hydrogenating catalyst, and the obtained gaseous hydrocarbon, containing the $^3H$ content of the sample in chemically bonded form in a reduced volume, is fed directly into the detecting unit as a counting gas. In such instances chemical reactions resulting in the decrease of mole number are particularly advantageous, since they substantially reduce the volume of the sample.

According to another preferred process variant oxygen and hydrogen, necessary for the preparation of the gas sample, are prepared in situ in an electrolyzing cell. Due to the high current density required for this process ozone is also formed in a substantial amount, which promotes the quick and quantitative burning of the substances. By varying the voltage of the cell the gas flow rate can be controlled with a high accuracy.

In compliance with a further advantageous method of the process according to the invention the sequence of the gas sample preparation steps and the continuity of the operation without manual intervention are ensured by controlling with a time programming, unit adjustable as required, an electromechanically or pneumatically operated feeding unit and gas valves.

This invention relates further to equipment for carrying out the above process, comprising a feeding unit, a burning unit connected to said feeding unit and serving for converting the hydrogen content of the sample into water and the carbon content of the sample into a gas, a reactor connected to said burning unit, charged with a contact capable of isolating the tritium content of the water and converting the same into gas, one or more detecting unit(s) connected to said reactor, and one or more recording unit(s) connected to said detecting unit(s).

The equipment preferably contains also an electrolyzing cell, connected to the burning unit and to the reactor, for the production of hydrogen and oxygen gases.

When the isotope content of a sample containing $^{14}C$ is to be determined, the equipment may comprise also a reactor, charged with a contact for removing the oxygen content of the gas, attached to the reactor and to the electrolyzing cell, as well as a water separating unit attached to the oxygen-removing reactor and to the detecting unit(s).

FIG. 3 shows an operation program referring to the operation of an advantageous variant of the equipment according to the invention.

Figure 1:
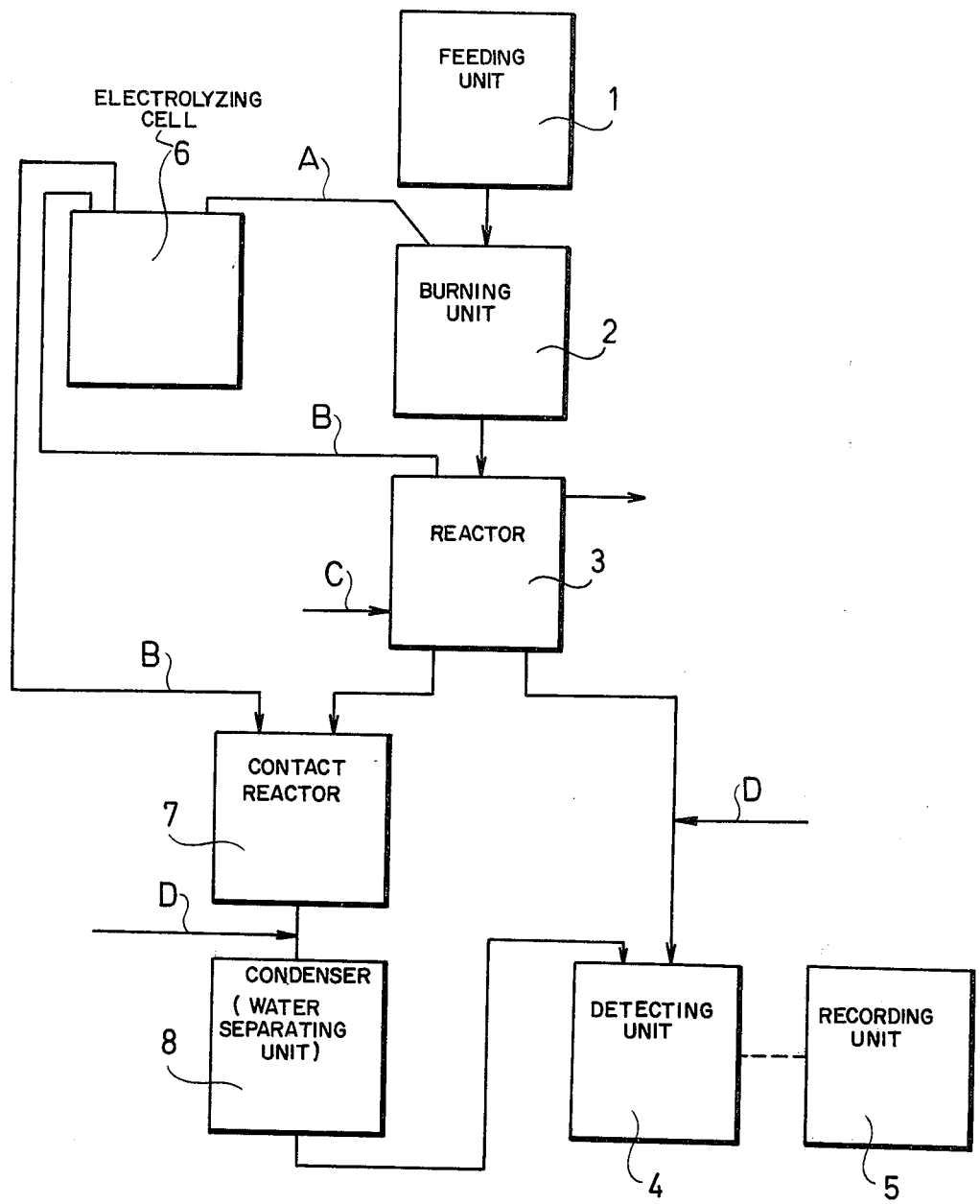
FIG. 1 shows the block diagram of the equipment according to the invention.

The equipment according to the invention as well as its operation is described below with reference to FIG. 1.

The sample is fed into chamber 2 by feeding unit 1, wherein the sample is burnt in order to convert its hydrogen content into water and its carbon content into a gas, preferably into carbon dioxide. The gas is passed into reactor 3 by means of oxygen flow, where tritium is bonded on the surface of a contact containing activated hydrogen and capable of water retention or adsorption, preferably on the surface of aluminium oxide and/or aluminium hydrosilicate catalyst. The gases formed in the burning process are removed from reactor 3 by oxygen flow, and the reactor is flushed with an inert gas flow, preferably with nitrogen. Thereafter the tritium bonded on the surface of the catalyst charged into reactor 3 is continuously converted into gas using a flow of gas capable for tritium exchange, preferably a hydrogen flow, and the obtained gas encompassing the total $^3H$ content of the sample is fed into detecting unit(s) 4 together with a counting gas, preferably with a propane-butane mixture. Detecting unit(s) 4 are in connection with recording unit 5, which may be used optionally also for data storage.

Oxygen and hydrogen are preferably prepared in electrolyzing cell 6.

When determining the isotope content of a sample containing also $^{14}C$ isotope, the gas mixture leaving reactor 3 is passed by oxygen flow into reactor 7 where the $O_2$ content of the gas mixture is reacted on an appropriate contact, preferably on a charge of Cu—CuO, with hydrogen to yield water vapour. The gaseous sample together with this water vapour is forwarded into condenser 8, where the water vapour condenses. Between reactor 3 and detecting unit 4 a carrier gas, preferably a mixture of propane and butane, is introduced into the gas transport, thereby forwarding the gas encompassing the total $^{14}C$ content of the sample into detecting unit 4.

Gas conduits A, B, C and D connect the oxygen, hydrogen, nitrogen and counting gas sources with the system.

The communication between the individual parts of the equipment is controlled preferably by valves of automatic operation. The sequence of the operation of the valves is controlled by a programming unit.

The main advantages of the process and equipment according to the invention are as follows:

1. In all of the cases the measurement is carried out in the same gas phase, accordingly the determination of the isotope content of widely different samples containing $^3H$ (e.g. biological samples, etc.) can be carried out under identical conditions.

2. The counting efficiency is nearly 100 % and is constant even in such cases when both the $^3H$ and $^{14}C$ content of the sample are to be determined. The high and steady counting efficiency can be attributed to the quantitative separation of the $^3H$ and $^{14}C$ content of the sample. The results obtained by the process according to the invention can be evaluated directly, no correction calculations are necessay, and expensive computers need not to be used.

3. The equipment supplies accurate results with good reproducibility. The accuracy and reproducibility of the measurement is independent of the skill and training of the operator.

4. No separate operations are required for sample preparation, and the conversion of a sample into counting gas proceeds continuously and automatically without any manual intervention, apart from placing the sample into the feeding unit. Consequently, the capacity of the equipment is very high, and its handling is very simple.

5. Due to its simple design, the equipment is not expensive, the chance for breakdowns is low, and its maintenance can easily be carried out.

6. The memory effect of the equipment is practically nil, in contrast with the know gas-phase measuring processes. This is particularly important in the measurement of $^3H$ activity, where up to now the memory effect could practically not be excluded.

7. Since measurements are carried out in identical chemical form, the equipment can easily and very accurately be tested with standard samples.

8. The detecting unit can be operated at room temperature and atmospheric pressure, so no expensive vacuum pumps, cooling or conditioning means are required.

Figure 2:
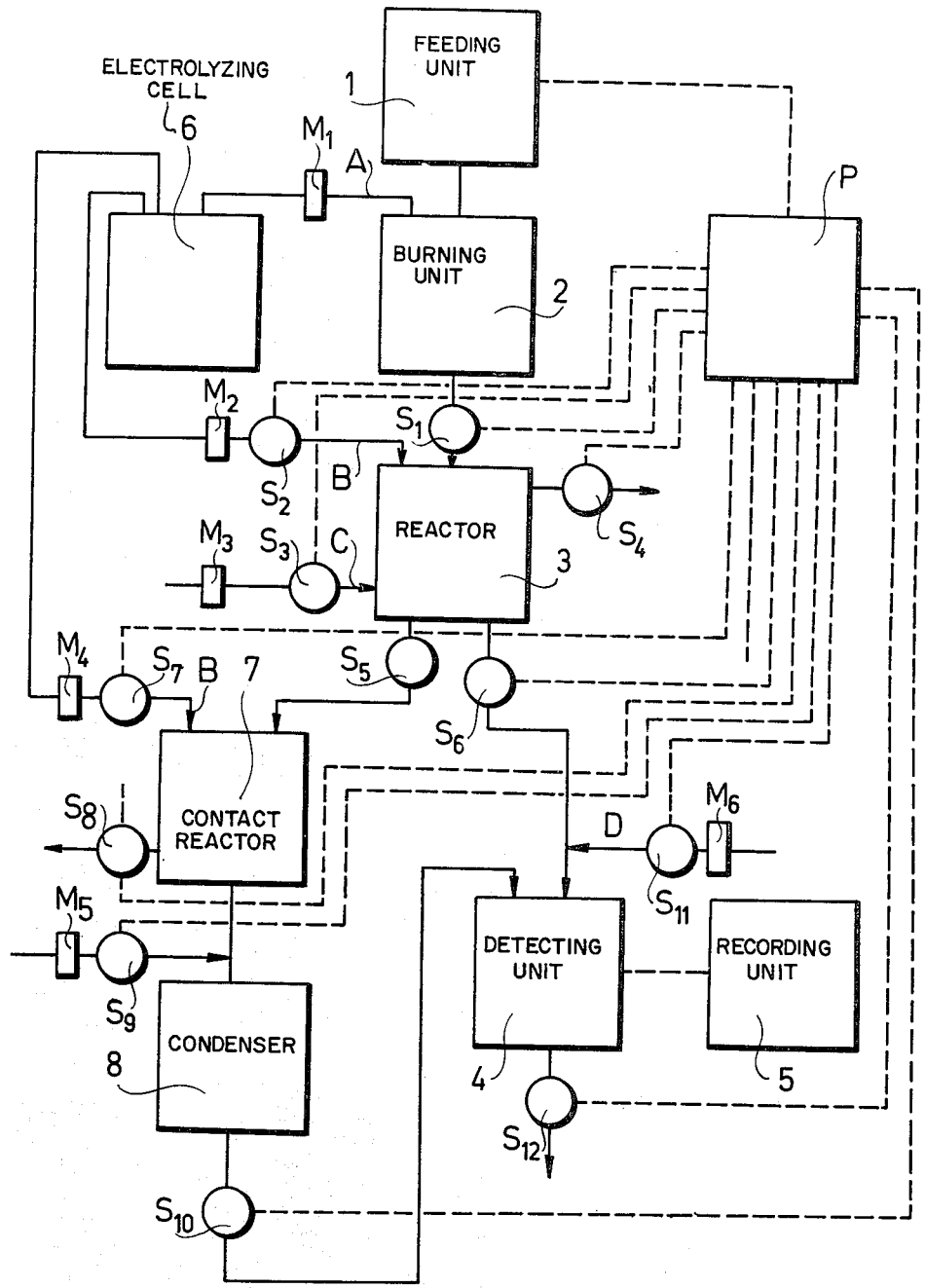
FIG. 2 shows the block diagram of an advantageous variant of the equipment according to the invention.

An advantageous variant of the process according to the invention as well as the operation of an advantageous form of the equipment are described in the following Example, with reference to FIGS. 2 and 3, respectively.

EXAMPLE

Samples of $^3H$ and $^{14}C$ content placed into sample holders made of aluminium foil, are placed into feeding unit 1. Upon a pulse produced by programming unit P the feeding unit drops the first sample into burning chamber 2 made of quartz or metal, heated to 900 °C, and filled with oxygen arising from electrolyzing cell 6 and fed into the chamber via conduit A through liquid level control $M_1$. The sample is completely burnt in this chamber within 30 to 60 seconds. One minute past the time of dropping, valves $S_1$, $S_5$, $S_7$, $S_9$, $S_{10}$ and $S_{12}$ open and the oxygen flow passes the $^3H$ containing water vapour as well as the $^{14}C$ containing carbon dioxide formed in the burning operation into reactor 7 through reactor 3. In reactor 3, charged with aluminium oxide - aluminium hydrosilicate catalyst and heated to 550 °C, tritium is bonded to the surface of the catalyst. In reactor 7 the gas stream is mixed with hydrogen fed into the reactor from electrolyzing cell 6 through pressure control $M_4$ and conduit B, and at the same time the oxygen content of the gas is converted to water vapour on the surface of the Cu—CuO contact heated to 600 °C. Propanebutane gas stream, which forwards the radioactive carbon dioxide into counting tube 4, is fed into the system through pressure control $M_5$ and conduit D. At the same time the water vapour formed in reactor 7 is condensed in water separator 8.

The activity measurement (counting) takes 2 min.; during this time all the valves are closed. During the same period reactor 3 is flushed with nitrogen introduced through pressure control $M_3$ and conduit C.

The counting tube operates in the proportional range, at a working point 4700 V. The background radiation is eliminated by circular anticoincidence technique and a lead shield of 5 cm. thickness. The electric signals produced by the counting tube are recorded by a two-channel coincidence counter 5. The third channel reduces the signals coming from the internal tube by the pules arriving in coincidence. The recording unit writes the pules arriving from the individual channels onto a tape.

After the measurement of $^{14}C$ activity, the counting tube is decontaminated by means of a propane butane mixture introduced through manostate $M_5$ while valves $S_9$, $S_{10}$ and $S_{12}$ are open. Thereafter the tritium bonded on the surface of the catalyst maintained at 550°C temperature in reactor 3 is continuously converted into gas by a hydrogen flow led from electrolyzing cell 6 through manostate $M_2$ and conduit B, and this active gas is flushed into counting tube 4 while valves $S_2$, $S_6$, $S_{11}$ and $S_{12}$ are open.

Thereafter the above-listed valves are closed and the activity of the gas mixture containing $^3H$ isotope is determined. At the same time reactor 3 is flushed with nitrogen led through the open valves $S_3$ and $S_4$ and manostate $M_3$ built into conduit C. When the activity measurement is finished, valves $S1$, $S_5$, $S_{11}$ and $S_{12}$ are opened. The nitrogen is removed from the system through valve $S_8$ with a flow of oxygen fed into reactor 7 through burning chamber 2 and reactor 3, and at the same time the charge of reactor 7 is regenerated. In the same phase counting tube 4 is decontaminated by a propane-butane mixture fed through manostate $M_6$ and conduit D.

Accordingly, the measurement takes place in seven stages, according to the time program shown in FIG. 3. In the diagram shadowed squares indicate closed valve positions, while blank squares indicate open valves; Roman numbers denote the operation stages; $S_1$, $S_2$ . . . $S_{12}$ denote the valves corresponding to the notation of FIG. 2.

| | Operation stage | Time |
|---|---|---|
| I. | Burning | 1 min. |
| II. | Separation of tritium, flushing | 2 min. |
| III. | Measurement of $^{14}C$, flushing with nitrogen | 2 min. |
| IV. | Decontamination | 1 min. |
| V. | Isotope exchange | 2 min. |
| VI. | Measurement of $^3H$, flushing with nitrogen | 2 min. |

-continued

| | Operation stage | Time |
|---|---|---|
| VII. | Regeneration of catalyst, de-contamination | 1 min. |

The above seven stages may be repeated without any manual intervention until there are no samples remaining in the feeding unit 1.

The results of a series of measurements proving the reproducibility of the process and the reliability of the operation of the equipment are given in Tables 1 and 2. Data listed in Table 1 refer to samples containing only $^3H$ isotope, while those given in Table 2 relate to samples containing both $^3H$ and $^{14}C$ isotopes.

Table 1

| No. | Sample | Net weight mg. | Activity cpm. | Background cpm. | Difference of activity and background cpm./mg. |
|---|---|---|---|---|---|
| 1. | Benzoic acid-4$^3H$ | 6.4 | 57.050 | 71 | 8.843 |
| 2. | Benzoic acid-4$^3H$ | 5.3 | 47.122 | 71 | 8.820 |
| 3. | Benzoic acid-4$^3H$ | 9.1 | 80.653 | 71 | 8.792 |
| 4. | Benzoic acid-4$^3H$ | 11.0 | 97.702 | 71 | 8.811 |
| 5. | Benzoic acid-4$^3H$ | 7.2 | 64.087 | 71 | 8.830 |
| 6. | Deoxy-D-ribose-2½$^3H$ | 11.2 | 28.235 | 83 | 2.438 |
| 7. | Deoxy-D-ribose-2½$^3H$ | 17.4 | 44.917 | 83 | 2.451 |
| 8. | Deoxy-D-ribose-2½$^3H$ | 21.0 | 52.353 | 83 | 2.410 |
| 9. | Deoxy-D-ribose-2½$^3H$ | 16.8 | 42.437 | 83 | 2.443 |
| 10. | Deoxy-D-ribose-2½$^3H$ | 14.0 | 34.790 | 83 | 2.402 |
| 11. | Blood | 22.2 | 34.654 | 76 | 1.485 |
| 12. | Blood | 24.5 | 40.817 | 76 | 1.590 |
| 13. | Blood | 30.5 | 16.775 | 78 | 472 |
| 14. | Blood | 26.0 | 12.064 | 78 | 386 |
| 15. | Urine | 6.2 | 44.628 | 84 | 7.114 |
| 16. | Urine | 10.5 | 79.580 | 84 | 7.485 |
| 17. | Liver | 14.1 | 207.270 | 70 | 14.630 |
| 18. | Liver | 14.5 | 205.494 | 70 | 14.102 |
| 19. | Liver | 22.0 | 62.678 | 72 | 2.777 |
| 20. | Liver | 26.3 | 67.933 | 72 | 2.511 |

Table 2

| No. | Sample | Net weight mg. | Activity $^{14}C$ cpm. | Activity $^3H$ cpm. | Background cpm. | Difference of activity and background ($^{14}C$) cpm./mg. | Difference of activity and background ($^3H$) cpm./mg. |
|---|---|---|---|---|---|---|---|
| 1. | Benzoic acid 7-$^{14}C$-4-$^3H$ | 7.1 | 8.563 | 133.622 | 80 | 1.126 | 18.740 |
| 2. | Benzoic acid 7-$^{14}C$-4-$^3H$ | 10.4 | 12.688 | 195.738 | 80 | 1.140 | 18.741 |
| 3. | Benzoic acid 7-$^{14}C$-4-$^3H$ | 12.0 | 14.292 | 226.464 | 80 | 1.111 | 18.792 |
| 4. | Benzoic acid 7-$^{14}C$-4-$^3H$ | 8.2 | 9.955 | 154.439 | 80 | 1.134 | 18.754 |
| 5. | Benzoic acid 7-$^{14}C$-4-$^3H$ | 8.6 | 10.458 | 161.938 | 80 | 1.136 | 18.770 |
| 6. | Blood | 26.8 | 24.736 | 372.600 | 81 | 842 | 13.822 |
| 7. | Blood | 25.0 | 24.150 | 352.175 | 81 | 885 | 14.006 |
| 8. | Blood | 22.6 | 15.707 | 230.430 | 84 | 611 | 10.112 |
| 9. | Blood | 27.2 | 21.053 | 285.872 | 84 | 690 | 10.426 |
| 10. | Liver | 18.4 | 27.802 | 145.250 | 76 | 1.435 | 7.818 |
| 11. | Liver | 16.0 | 26.336 | 127.712 | 76 | 1.570 | 7.906 |

What we claim is:

1. A process for measuring the $^3H$ and $^{14}C$ isotope content of substances in the gas phase, which comprises converting the hydrogen content of the substance into water and the carbon content into carbon dioxide in simultaneous oxidation processes, separating the resulting water from the resulting carbon dioxide by passing them through a contact catalyst capable of retaining water and containing activated hydrogen and thereby bonding the $^3H$ content of the water, purifying the separated gas which contains $^{14}CO_2$, transfering the purified gas with a counting gas into a detector unit, then continuously converting the $^3H$ retained by said contact catalyst to a gas by exchange reaction with a flowing gas, and feeding the thus liberated $^3H$-containing gas with a counting gas into a detectng unit.

2. The process of claim 1, wherein said activated hydrogen-containing contact catalyst is aluminum oxide, aluminum hydrosilicate, or a mixture of aluminum oxide and aluminum hydrosilicate.

3. The process of claim 1, wherein said conversion by exchange reaction is carried out with a hydrogen flow.

4. The process of claim 1, wherein said counting gas is a gaseous hydrocarbon or a mixture of gaseous hydrocarbons.

5. Apparatus for measuring the isotope content of a sample labeled with a $^3H$ isotope or a $^3H$ isotope and a $^{14}C$ isotope, comprising a feeding unit, a burning unit connected from said feeding unit for converting the hydrogen content of the sample into water and any carbon content of the sample into a carbonaceous gas, a reactor connected from said burning unit, said reactor being charged with a contact catalyst for isolating the $^3H$ content of the water and converting it into a gas, at least one detecting unit connected from said reactor, and at least one recording unit connected from said detecting unit.

6. The apparatus of claim 5, further comprising an electrolyzing cell connected from said burning unit and from said reactor for the production of hydrogen and oxygen gases.

7. The apparatus of claim 6 for use when said sample also contains a $^{14}C$ isotope, the apparatus further comprising a second reactor connected from said reactor, said second reactor being charged with a contact catalyst for removing the oxygen content of the gas, said second reactor being further connected from said electrolyzing cell, and a water separating unit connected from said second reactor and from said detecting unit.

* * * * *